United States Patent [19]
Violay et al.

[11] Patent Number: 6,048,537
[45] Date of Patent: Apr. 11, 2000

[54] METHOD FOR PREPARING AN INFLUENZA VIRUS, ANTIGENS OBTAINED AND APPLICATIONS THEREOF

[75] Inventors: Jean Michel Violay, Francheville; Guy Court, Saint-Pierre-la-Palud; Catherine Gerdil, Ecully; Herve Chalumeau, Charbonnieres, all of France; Patric McVerry, Stroudsburg, Pa.

[73] Assignee: Pasteur Merieux Serums et Vaccins, France

[21] Appl. No.: 08/793,373

[22] PCT Filed: Jun. 6, 1995

[86] PCT No.: PCT/FR95/00727

§ 371 Date: May 27, 1997

§ 102(e) Date: May 27, 1997

[87] PCT Pub. No.: WO96/05294

PCT Pub. Date: Feb. 22, 1996

[30] Foreign Application Priority Data

Aug. 16, 1994 [FR] France ................... 94 10039

[51] Int. Cl.[7] .......................... A61K 35/145; C12N 7/02; C12N 7/06
[52] U.S. Cl. ................... 424/209.1; 424/210.1; 435/235.1; 435/326; 435/329
[58] Field of Search .................... 424/78.1, 235, 424/236, 238, 209.1, 210.1; 435/235.1, 238, 239; 530/412

[56] References Cited

U.S. PATENT DOCUMENTS

| | | | |
|---|---|---|---|
| 4,000,257 | 12/1976 | Cano et al. | 424/89 |
| 4,057,626 | 11/1977 | Metzgar et al. | 424/89 |
| 4,064,232 | 12/1977 | Bachmayer et al. | 424/89 |
| 4,327,182 | 4/1982 | Benedictus . | |
| 4,356,169 | 10/1982 | Simons et al. | 424/89 |

FOREIGN PATENT DOCUMENTS 9213002 8/1992 WIPO .

OTHER PUBLICATIONS

Phelan, et al (1980) J. Biological Standards, vol. 8, (pp. 233–242). Purification of influenza virus glycoproteins for the preparation . . . .

Gruschkau, et al (1973) Purification of influenza virus. (in) Series Immun Biol Standard, vol. 20, pp. 79–84 (Karger, Busel) Symposium Ser. Immunobiol. Stand.

*Primary Examiner*—Mary E. Mosher
*Attorney, Agent, or Firm*—Bierman, Muserlian and Lucas

[57] ABSTRACT

Method for preparing purified influenza antigens from a fluid containing influenza virus, comprising the steps of concentration, purification, fragmentation and, where appropriate, inactivation, characterized in that:

A. either the purification step entails several ultracentrifugation steps separated by a filtration step, B. or the fragmentation step is performed on the live virus in the presence of an amphiphilic nonionic detergent, followed by a removal of undesirable substances by filtration, retaining all of the viral constituents, or these two steps are carried out in any order.

12 Claims, No Drawings

METHOD FOR PREPARING AN INFLUENZA VIRUS, ANTIGENS OBTAINED AND APPLICATIONS THEREOF

The invention relates to a method for the fragmentation of live influenza virus, which is simple to carry out, leads to a destruction of the infectious power and can be used, in particular, in the manufacture of an inactivated influenza vaccine or for obtaining viral antigens for diagnostic purposes.

The influenza virus or flu virus is an enveloped, single-stranded RNA virus with helical symmetry, belonging to the family Orthomyxoviridae. The known antigens are essentially represented by the following structural proteins:

NP: Capsid nucleoprotein linked to the viral RNA

M: Envelope protein "matrix"

PA: Polymerases linked to the viral RNA

HA: Protein haemagglutinin located at the surface of the envelope

NA: Neuraminidase surface enzyme protein

The nucleoprotein and the M protein are the internal antigens specific to the viral types A and B, the haemagglutinin and the neuraminidase determining the virus A subtypes.

The haemagglutinin is the most immunogenic glycoprotein of the viral constituents. The haemagglutinin content is used to express the load of viral antigens in influenza vaccines; nevertheless, it is now established that all of the viral antigens participate in the stimulation of the immune response, and that the internal antigens play a major part in the cell-mediated response.

The nucleoprotein (NP) is the main target antigen of cytotoxic T lymphocytes (CTL), no CTL specific for the haemagglutinin having been detected in man.

Viral fragmentation enables the envelope to be ruptured and all of the NP, M, RNA, viral polymerase, HA and NA viral antigenic sites to be released.

Vaccines obtained by this method are hence extremely immunogenic and give larger seroconversions than those obtained with vaccines containing only the surface antigens (which represent ony 36% of the viral constituents).

Vaccines containing fragmented virions are also better tolerated than vaccines containing whole virions, which are more allergenic.

The fragmentation methods used combine solvent-detergent treatments such as polysorbate/anaesthetic ether or polysorbate/chloroform [Pasteur Institute (Adamowicz-Muller) U.S. Pat. No. 4,522,809].

The implementation of these methods on an industrial scale necessitates suitable premises and equipment, such as flameproof installations in the case of ether and specific protection for the operators with respect to the neurotropic toxicity of chloroform.

Other methods employ detergents or proteolytic enzymes or bile salts, applied to previously inactivated viruses. These methods are essentially used for obtaining surface subunits (HA and NA) in the manufacture of subunit vaccines lacking the internal antigens. Examples which may be mentioned include the use of sodium deoxycholate described in Patent DD 155875, that of surfactants described in U.S. Pat. No. 4,327,182, and lastly that of nonionic detergents described in Patent FR 2,483,779.

Our method, which is simple to carry out, enables the fragmentation of purified live influenza virus to be performed without a solvent at room temperature. This method comprises the removal of the detergent and of undesirable substances, enabling the viral fragmentation product to be obtained in a fully defined, isotonic, buffered ionic environment.

This method leads to a very considerable reduction in the infectious titre of the purified influenza virus suspension, which can go as far as complete inactivation, depending on the working conditions adopted, such as the concentration and contact time between detergent and influenza virus.

Hence the subject of the present invention is a method for preparing purified influenza antigens from a fluid containing influenza virus, comprising the steps of concentration, purification, fragmentation and, where appropriate, inactivation, characterized in that:

A. either the purification step entails several ultracentrifugation steps separated by a filtration step, B. or the fragmentation step is performed on the live virus in the presence of an amphiphilic nonionic detergent, followed by a removal of undesirable substances by filtration, retaining all of the viral constituents, or these two steps are carried out in any order.

In a preferred embodiment of the method, the influenza virus used is obtained by culture on sensitive host cells, such as mammalian cells, namely monkey, hamster or pig kidney cells or ferret or mouse cells, or cells originating from embryos, from human pulmonary tissue or from chick embryo fibroblasts.

The commonest system for the industrial production of vaccine is the embryonate chicken egg; this is the preferred system.

Hence the subject of the present invention is also the method as described above, characterized in that the influenza virus is obtained by culture on embryonate eggs.

The fertilized eggs must be carefully selected and must originate from healthy farms reserved for this production.

They are placed in an incubator at 37.8° C. (100° F.) for 9 to 12 days; embryonic development and embryo vitality are checked by candling before inoculation of the influenza virus into the allantois.

The eggs are then incubated for 2 to 3 days in temperature- and humidity-controlled culture incubators so as to effect viral infection under optimal conditions. These conditions vary according to the influenza strains and viral seeds used. Incubation is stopped by rapid refrigeration at 5±3° C. The allantoic fluid, very rich in viral particles, is then withdrawn from the infected eggs.

The virulent allantoic fluid is thus obtained, and it must be rapidly purified in order to remove the impurities present: proteins including ovalbumin, lecithins, bacteria, and the like. The harvested material is clarified by centrifugation and concentrated up to 20 times by ultrafiltration prior to viral purification.

The viral purification operations known to a person skilled in the art make use of separating techniques such as filtration, ultracentrifugation or affinity chromatography. These operations bring about a concentration of the influenza virus.

In point of fact, we have found that it is preferable to perform the purification on the live influenza virus, it being possible for inactivation prior to purification to give rise to a large amount of irreversible chemical bridging between viral proteins and impurities, which are detrimental to the efficacy of the purification operations. For this reason, our invention comprises the obtaining of live purified influenza virus.

The purification technique which is the subject of the present method is based on zonal ultracentrifugation. This ultracentrifugation is preferably carried out on a density gradient, preferably on a sucrose gradient but it is also possible to use a caesium chloride gradient. The centrifugation is performed at an acceleration which is preferably of the order of 90,000 g; the said centrifugation may be performed in continuous fashion or in successive batches. A separation of viral particles in accordance with their size, their density and their shape is thus achieved. Only the gradient fractions containing the virus are taken.

Depending on the type of rotor used, a dynamic harvesting (during centrifugation) or static harvesting (at rest) after reorientation of the gradient will be performed.

The method which is the subject of the present application entails a sequence of several ultracentrifugation steps, preferably two successive steps separated by a filtration step. Filtration step is understood to mean either a single filtration, or a sequence of several filtrations of which the last one can be of the order of 0.3 µm and preferably of approximately 0.5 µm, for example 0.45 µm.

This sequence, applied to live influenza virus, effects a reproducible industrial purification of strains of influenza viruses cultured on embryonate eggs.

Before the viral fragmentation step, the suspension of concentrated purified virus is optionally standardized by dilution to constant optical density (OD) values indicating the viral protein content of the sample to be treated. The final concentration can, for example, preferably be between 200 and 1,000 µg of proteins per ml. Dilution is preferably performed using a sterile buffer, for example PBS (phosphate buffered saline).

Hence the subject of the invention is also a method as described above, characterized in that, between the purification step and the fragmentation step, a step of standardization by adjustment of protein concentration is performed.

Viral fragmentation is performed at room temperature (20–25° C.) by adding an amphiphilic nonionic detergent to the purified and, where appropriate, standardized suspension of live virus. This detergent is preferably a product having the general formula $$R-\text{C}_6\text{H}_4-(O-CH_2CH_2)_nOH$$

in which R represents an octyl or nonyl radical and n represents an integer equal to or greater than 3.

Among the products covered by the general formula above, the following commercial products may be mentioned: Triton X-100®, Triton X-165®, Triton X-205®, Triton X-305® or Triton X-405®.

More especially, the amphiphilic nonionic detergent which is preferably used is Triton X-100 or octoxinol 9.

The fragmentation reaction takes place with stirring, for example during at least one hour of contact, but it is possible to continue it for a much longer time, for example up to 24 hours. The fragmentation is normally performed in a controlled-environment area at room temperature.

During this operation, the viral structure is dissociated. The viral envelope is ruptured, releasing into the medium the internal constituents, especially the NP and M antigens, the only antigens known to be involved in the cell-mediated immune response. A portion of the surface antigens (HA, NA) is also released. Studies of the particle size profile after treatment show that the viral suspension contains almost exclusively nothing other than the fragmented virus, thereby satisfying, for example, the criteria of the European Pharmacopoeia for fragmented influenza vaccines for human use.

The fragmentation is stopped by removal of the detergent.

The technique of removal of undesirable substances employs a filter membrane whose porosity permits the passage of detergent molecules and other non-viral solutes and retains the viral fragmentation product.

The choice of membrane is guided by the size and molecular weight of the smallest free antigenic units.

The free haemagglutinin is a trimer of MW 210 kilodaltons (monomer: 70 kilodaltons). The operation is carried out by tangential filtration through a membrane of porosity less than or equal to 100 kilodaltons, preferably approximately 50 kilodaltons, and the sample is diafiltered during this ultrafiltration with 10 to 30 volumes of sterile isotonic buffer, preferably PBS.

Hence the subject of the invention is a method as described above, characterized in that the step of removal of undesirable substances is performed according to a diafiltration method permitting washing of the suspension of fragmented virus with a buffer solution employing a filter membrane retaining the larger part of the viral constituents.

After diafiltration, which results in the removal of undesirable substances, the suspension of fragmented virus is concentrated to a desired volume, which may be matched to a standard viral concentration by OD measurement.

Viral inactivation tests performed following this treatment show that the fragmentation method causes a very considerable fall in the infectious titre of the suspension of purified virus, which can go as far as complete inactivation of the influenza virus irrespective of the viral type (A or B).

Hence the subject of the invention is also a method as described above, characterized in that the fragmentation step is carried out under conditions permitting complete inactivation of the purified influenza virus.

Viral inactivation can, if appropriate, be completed by adding, if necessary, an inactivating agent (formaldehyde, β-propiolactone) according to techniques known to a person skilled in the art.

A preservative and any other additive (adjuvant) may optionally be added to the vaccine obtained.

The subject of the invention is also a method as described above, characterized in that it is carried out either according to step A, or according to both steps A and B.

The subject of the invention is also a method for preparing purified influenza antigens from a concentrated allantoic fluid containing live influenza virus, characterized in that:

the viral concentrate is purified by zonal ultracentrifugation, preferably on a sucrose gradient, the harvested material obtained is filtered, preferably up to a pore size of not less than 0.3 µm, and the ultracentrifugation operation is then repeated;

the purified viral suspension is standardized by dilution in an aqueous buffer;

the standardized product is fragmented by adding octoxinol 9, and a removal of undesirable substances is then performed by diafiltration employing an ultrafiltration using a buffer solution;

and an inactivation of the viral suspension is performed if necessary and if desired, preferably using formaldehyde.

The subject of the present invention is also, by way of medicinal products, the viral fragments as obtained according to the method described above, as well as the application of the purified influenza antigens as obtained according to the method described above to the preparation of an influenza vaccine for human or veterinary use, and lastly the application of the purified influenza antigens as obtained according to the method described above to the preparation of products which can be used for diagnostic purposes.

The preparation of vaccines and diagnostic tests embracing the influenza antigens as obtained according to the method described above may be carried out according to methods known to a person skilled in the art.

The method which constitutes this invention is illustrated by means of the example which follows, which cannot be considered to limit the protection of the said invention.

EXAMPLE

1. Viral Culture

The strain A/H3N2 A/Beijing 32/92×117 is inoculated into 11-day embryonate eggs placed in incubation for 72 hours at 35° C.

The harvested allantoic fluid is clarified by centrifugation and filtration.

The clarified allantoic fluid is then concentrated by ultrafiltration and stabilized in citrate buffer.

2. Purification

The viral concentrate is purified by zonal ultracentrifugation in a sucrose gradient (10 to 55%) at 35,000 rpm. The procedure is performed as a continuous-flow operation.

The viral fractions harvested from the gradient represent approximately 800 ml. The sucrose concentration is in the region of 40%. This harvested material is filtered up to 0.45 $\mu$m; the final volume of suspension, after rinsing of the filters, is equal to 15 litres.

The ultracentrifugation step is carried out again according to the same working conditions.

3. Viral Fragmentation

After the second purification, the suspension of purified virus (1010 ml) is standardized by dilution in sterile PBS buffer so as to obtain a protein concentration of between 200 and 1,000 $\mu$g/ml.

After standardization, the volume of the viral suspension is 2000 ml. The infectious titre is greater than $10^{10} ID_{50}$/ml.

Viral fragmentation is performed by the aseptic addition of 10 ml (0.5% vol./vol.) of octoxinol 9 (Triton X-100) with magnetic stirring at laboratory temperature.

After one hour of contact, the viral suspension, which exhibits flocculation, is clarified by centrifugation. Diafiltration is carried out aseptically to a constant sample volume by ultrafiltration through a 50 kD membrane, using a volume of isotonic phosphate buffer (PBS) equal to 20 litres.

On completion of the diafiltration, the sample is free from detergent and sucrose (100-fold reduction). The infectious titre, after fragmentation, is reduced to $10_{1.2} ID_{50}$/ml, representing a decrease by a factor of more than $10^9$, achieved for one hour of treatment.

In other experiments, it was possible to obtain a complete inactivation of the fragmented viral suspension by means of extended (>2 hours) virus/detergent contact times.

In the present example, inactivation was completed by adding formaldehyde (0.01% vol./vol.).

The vaccine obtained was filtered through 0.2 $\mu$m and merthiolate (0.01% weight/vol.) was added. This experiment enabled 13,000 ml of A/Beijing 32/92×117 monovalent vaccine titrating at 137 $\mu$g of HA/ml to be produced.

The quality of the antigens obtained, evaluated by verification of the immunological integrity of the haemagglutinin and neuraminidase proteins, complies with international specifications (European Pharmacopoeia).

Moreover, the vaccinating properties of the preparations, verified by administration to man and animals (mice), made it possible to obtain seroconversions inducing an immunological protection, according to the criteria of clinical evaluation of influenza vaccines.

We claim:

1. A method of preparing a purified mixture of influenza viral antigens containing surface and internal antigens, said method comprising the following successive steps: concentrating a fluid containing influenza virus, purifying the resulting concentrate, fragmenting the live virus in the purified concentrate, and optionally inactivating the fragmented mixture wherein A) either the purification step comprises at least one sequence comprising in successive order a first ultracentrifugation followed by a filtration followed by a second ultracentrifugation, said first and second ultracentrifugation and said filtration are carried out on live viral particles, or B) the fragmentation of the live virus is effected in the presence of an amphiphilic nonionic detergent followed by filtration to remove non-influenza viral substances, including said detergent, while retaining all the viral influenza antigens, or steps A and B are both carried out in order.

2. The method of claim 1 comprising both steps A and B.

3. The method of claim 1 wherein the said detergent is octoxinol 9.

4. The method of claim 1 wherein the purified virus is standardized by dilution to between 200 and 1000 $\mu$g of protein per ml before the fragmentation step.

5. The method of claim 1 wherein the filtration of step B is dialfiltration premitting washing of the suspension of fragmented virus with a buffer solution using a filter membrane to retain the larger part of viral antigens.

6. The method of claim 1 wherein the purification is effected by two zonal ultracentrifugations separated by filtration with a filter with a pore size of at least 0.3 $\mu$m to obtain purified material.

7. The method of claim 1 wherein the fragmenting step results in complete inactivation of the purified influenza virus.

8. The method of claim 1 wherein the influenza virus has been cultured on embryonate eggs.

9. A method of preparing purified influenza antigens comprising A) concentration an allantoic fluid containing live influenza virus B) purifying the concentrated fluid by zonal ultracentrifugation followed by filtration which retains non-soluble, non-viral particulate material while letting the viral particulate material through the filter with a pore size of the order of 0.3 $\mu$m followed by a second zonal centrifugation to obtain a live purified viral suspension, C) standardizing the purified viral suspension by dilution with an aqueous buffer, D) fragmenting the standardized viral suspension by addition of octoxinal 9, E) subjecting the fragmented product to diafiltration using ultrafiltration with a buffer solution to remove undesired substances and F) optionally inactivating viral suspension.

10. The method of claim 9 wherein the zonal ultracentrifugation of step B is effected on a sucrose gradient and the inactivation of step F) is effected with formaldehyde.

11. A purified influenza antigen prepared by A) concentrating an allantoic fluid containing live influenza virus B) purifying the concentrated fluid by zonal ultracentrifugation followed by filtration which retains non-soluble, non-viral particulate material while letting the viral particulate material through the filter with a pore size of the order of 0.3 $\mu$m followed by a second zonal centrifugation to obtain a live purified viral suspension, C) standardizing the purified viral suspension by dilution with an aqueous buffer, D) fragmenting the standardized viral suspension by addition of octoxinol 9. E) subjecting the fragmented product to dialfiltration using ultrafiltration with a buffer solution to remove undesired substances and F) optionally inactivating viral suspension.

12. An influenza vaccine containing a purified influenza antigen prepared by A) concentrating an allantoic fluid containing live influenza virus B) purifying the concentrated fluid by zonal ultracentrifugation followed by filtration which retains non-soluble, non-viral particulate material while letting the viral particulate material through the filter with a pore size of the order of 0.3 $\mu$m followed by a second zonal centrifugation to obtain a live purified vial suspension, C) standardizing the purified viral suspension by dilution with an aqueous buffer, D) fragmenting the standardize viral suspension by addition of octoxinol 9. E) subjecting the fragmented product to dialfiltration using ultrafiltration with a buffer solution to remove undesired substances and F) optionally inactivating viral suspension.

* * * * *